United States Patent
Liu et al.

(10) Patent No.: US 10,160,965 B2
(45) Date of Patent: *Dec. 25, 2018

(54) METHOD AND MATERIALS FOR NUCLEIC ACIDS EXTRACTION AND PURIFICATION

(71) Applicants: Yiding Liu, Twinsburg, OH (US); Baochuan Guo, Solon, OH (US)

(72) Inventors: Yiding Liu, Twinsburg, OH (US); Baochuan Guo, Solon, OH (US)

(73) Assignee: GLC Biotechnology, Inc., Hudson, OH (US)

( * ) Notice: Subject to any disclaimer, the term of this patent is extended or adjusted under 35 U.S.C. 154(b) by 410 days.

This patent is subject to a terminal disclaimer.

(21) Appl. No.: 14/712,018

(22) Filed: May 14, 2015

(65) Prior Publication Data

US 2015/0353918 A1    Dec. 10, 2015

Related U.S. Application Data

(60) Provisional application No. 61/994,975, filed on May 18, 2014.

(51) Int. Cl.
| | |
|---|---|
| *C12Q 1/68* | (2018.01) |
| *C12P 19/34* | (2006.01) |
| *C12N 15/10* | (2006.01) |

(52) U.S. Cl.
CPC ..... *C12N 15/1013* (2013.01); *C12N 15/1003* (2013.01)

(58) Field of Classification Search
None
See application file for complete search history.

(56) References Cited

U.S. PATENT DOCUMENTS

| | | | |
|---|---|---|---|
| 3,119,812 A | 1/1964 | Peter et al. | |
| 3,382,229 A | 5/1968 | Patton et al. | |
| 4,051,317 A | 9/1977 | Towle | |
| 4,053,699 A | 10/1977 | Cahalan et al. | |
| 4,254,257 A | 3/1981 | Schroeck | |
| 6,090,628 A * | 7/2000 | Peck | C12N 9/10 435/270 |
| 2012/0083598 A1 * | 4/2012 | Suh | C12N 15/1017 536/25.42 |
| 2012/0208189 A1 * | 8/2012 | Xu | C07H 21/02 435/6.11 |

OTHER PUBLICATIONS

Ahern, The Scientist 9 (15), 20 (1995).*

* cited by examiner

*Primary Examiner* — James Martinell

(57) ABSTRACT

Provided herein is materials and method relating to nucleic acids extraction and purification from biological samples. In particular, a pre-treatment buffer is used to facilitate the extraction and purification of nucleic acids from biological samples, more specifically, removing inhibitors and impurities from biological samples and resulting in a highly concentrated and purified nucleic acids preparation.

5 Claims, 1 Drawing Sheet
Specification includes a Sequence Listing.

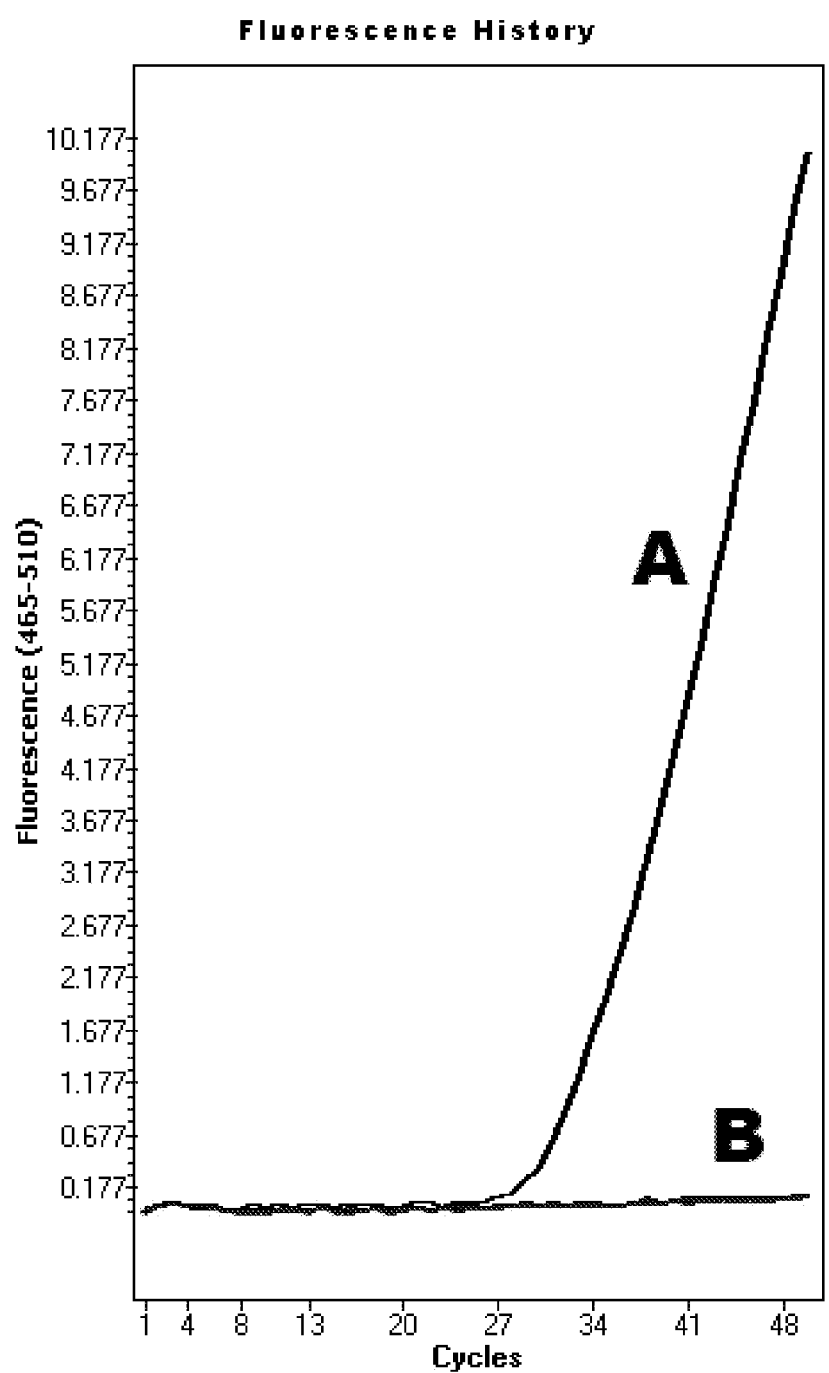

METHOD AND MATERIALS FOR NUCLEIC ACIDS EXTRACTION AND PURIFICATION

CROSS-REFERENCE TO RELATED APPLICATION

The present application claims priority to and the benefit of U.S. provisional patent application Ser. No. 61/994,975 filed May 18, 2014, the entire disclosure of which is incorporated herein by reference.

FIELD OF INVENTION

The invention relates generally to assays that analyze the nucleic acid biomarker for detecting cancer and other diseases, and more particularly, to extraction and purification of nucleic acids from samples containing nucleic acids for use in these assays.

BACKGROUND OF THE INVENTION

Nucleic acid-based testing is emerging as a promising method for detecting cancer and many other diseases. Retrieving highly purified nucleic acids from a clinical sample is an essential part of nucleic acid-based testing because it is based on analysis of the nucleic acid biomarker retrieved from the sample. In clinical specimen such as stool, the quantity of the nucleic acid biomarker is low and the biomarker may constitute only a small portion of total nucleic acids in a sample, meaning that detecting the rare biomarker requires the extraction of sufficient amounts of nucleic acids for enzymatic-based analysis. In other words, methods for nucleic acid extraction and purification must be able to effectively convert a large clinical sample to highly concentrated, highly purified nucleic acids so that enough amounts of the nucleic acid biomarker can be loaded for analysis.

Nucleic acid extraction and purification methods include alcohol precipitation, binding of nucleic acids to silica in the presence of chaotropic salts, gel filtration, ion exchange, and sequence-specific capture. However, when these methods are used alone, they are often not effective in preparation of highly concentrated, highly purified nucleic acids from clinical specimen, especially from a large clinical sample. This is because clinical specimen is highly complex and contains large amounts of interfering substances that can significantly reduce the effectiveness of nucleic acid extraction and purification methods, leading to a failure of recovering or detecting the nucleic acid biomarker from the clinical sample. For example, current methods are not effective in preparation of highly purified DNA from stool. Moreover, clinical sample contains a large amount of various inhibitors that could be co-isolated and concentrated with nucleic acids, inhibiting enzymatic-based analysis. As a result, their presence can limit the total quantity of nucleic acids that can be loaded for analysis because these inhibitors inhibit enzymatic-based analysis if their level is high in the system, leading to a failure of detecting the nucleic acid biomarker from the sample.

Pre-treating clinical specimen such as stool before nucleic acid extraction and purification is a means to reduce the effect of the interfering substances and inhibitors on extraction and detection of nucleic acids. The prior art pre-treatment methods include cetyl trimethylammonium bromide (CTAB) treatment, phenol/chloroform extraction, and protease treatment. These methods can be used either alone or in combination. However, these prior pre-treatment methods are not very effective when nucleic acids are extracted from a large clinical sample because of labor intensive protocols including multiple centrifugation and sample transfer steps.

Clearly, there is a need for methods that can effectively extract nucleic acids from a large clinical sample, while minimizing co-isolation of the inhibitors so that enough amounts of nucleic acids can be loaded (or used) for enzymatic-based analysis. The present invention addresses the issue associated with extraction and purification of nucleic acids from a sample containing nucleic acids, particularly from a large clinical sample.

SUMMARY OF THE INVENTION

The ability of isolating highly concentrated, highly purified nucleic acids from a sample containing nucleic acids, particularly from a large clinical sample is important to nucleic-acid-based testing. Accordingly, this current invention provides a pre-treatment buffer, a method, and a kit to extract highly concentrated, highly purified nucleic acids from a clinical sample. The technologies provided relate to processing and preparing nucleic acids by minimizing amounts of interfering substances and inhibitors. For example, the present invention provides technologies for removing interfering substances and inhibitors before nucleic acid extraction and purification so that the following nucleic acid preparation process can more effectively extract nucleic acids and minimize amounts of the inhibitors co-isolated.

This invention is particularly useful for fecal DNA testing, in which DNA retrieved from stool is detected. One application of fecal DNA testing is colorectal cancer screening. Fecal DNA testing is based on the detection of the DNA biomarker in stool by enzymatic-based analysis and therefore both the quantity and quality of extracted fecal DNA are essential to the analysis.

However, the technologies provided are not limited in the types of samples that can be processed by the buffer, method, and kit provided herein. This current invention is also useful for isolation of other nucleic acids such as various forms of RNA from sample.

In one embodiment, this invention provides a pre-treatment buffer for preparing purified nucleic acids. For example, provided herein is a pre-treatment buffer containing acetate salt(s) and reagent(s) for preparing purified nucleic acids from a sample containing nucleic acids, wherein said pre-treatment buffer is first mixed and incubated with said sample prior to nucleic acid extraction, leading to precipitation of the interfering substances and inhibitors (if present); then, said precipitates along with any solid matter (if present) are then pelleted by centrifugation, yielding more clarified supernatant containing nucleic acids; thereafter, the resulted supernatant is separated from pellets by transferring supernatant to another tube; finally, nucleic acids are extracted from the transferred supernatant by a nucleic acid extraction and purification method(s), yielding highly concentrated, highly purified nucleic acids for analysis.

In some embodiments, said acetate salt(s) in said pre-treatment buffer is one of the following or in combination, but not limited to, sodium acetate, potassium acetate, ammonium acetate, and lithium acetate; wherein the final concentration of said acetate salt(s) is 50 mM or more after mixing said buffer with said sample. In some embodiments, the final concentration of the acetate salt(s) is 100 mM or more after mixing said buffer with said sample. In some embodiments, the final concentration of the acetate salt(s) is 200 mM or more after mixing said buffer with said sample. In another embodiment, said reagent(s) in said buffer is one of the following or in combination, but not limited to, guanidine thiocyanate, guanidine chloride, urea, sodium chloride, potassium chloride, and phosphate salts; wherein the preferred final concentration of said reagent(s) is 1.0M or more after mixing said pre-treatment buffer with said sample. In some embodiments, the preferred final concentration of said reagent(s) is 2.0M or more after mixing said pre-treatment buffer with said sample.

In some embodiments, said sample is obtained from one of the following sources or in combination, but not limited to, human or animal tissues; cell cultures; bone marrow; human or animal body fluids such as blood, serum, plasma, urine, semen, cerebrospinal fluid, sputum, and smears; parts of plants, and plant extracts. In another embodiment, said sample is a stool sample containing nucleic acids.

In some embodiments, said nucleic acids are DNA, mRNA, tRNA, microRNA, siRNA, or any combination of them.

In some embodiments, said nucleic acid extraction and purification method is, but not limited to, carboxylate-modified magnetic beads capture, silica-based nucleic acid extraction and purification, and alcohol precipitation. In another preferred embodiment, said nucleic acid extraction and purification method is sequence specific capture with magnetic beads. In some embodiments, said pre-treatment buffer itself serves as a hybridization buffer for said sequence specific capture, eliminating a need for additional solution for hybridization.

The current invention also provides a method for preparing purified nucleic acids from a stool sample containing nucleic acids, the method comprises first mixing and incubating a pre-treatment buffer with the stool sample containing nucleic acid to precipitate the interfering substances and inhibitors in said stool sample (if present); then said precipitates along with any solid matter (if present) are pelleted by centrifugation, yielding more clarified supernatant containing nucleic acids; thereafter, said supernatant is separated from the pellets by transferring it to another tube; finally, nucleic acids are extracted and purified from the transferred supernatant by a sequence-specific capture method, yielding highly concentrated, purified nucleic acids for subsequent analysis.

In some embodiments, said pre-treatment buffer consists of acetate salt(s) and guanidine thiocyanate, wherein said acetate salt(s) is one of the following or in combination, but not limited to, sodium acetate, potassium acetate, ammonium acetate, and lithium acetate. The preferred final concentration of said acetate salt(s) is 50 mM or more after mixing said pre-treatment buffer with said stool sample. In some embodiments, the preferred final concentration of said acetate salt(s) is 100 mM or more after mixing said buffer with said stool sample. In some embodiments, the preferred final concentration of said acetate salt(s) is 200 mM or more after mixing said pre-treatment buffer with said stool sample. In some preferred embodiments, the final concentration of said guanidine thiocyanate is 1.0M or more after mixing said pre-treatment buffer with said stool sample. In one embodiment, the preferred final concentration of said guanidine thiocyanate is 1.0M or more after mixing said pre-treatment buffer with said stool sample. In another embodiment, the preferred final concentration of said guanidine thiocyanate is 2.0M or more after mixing said pre-treatment buffer with said stool sample.

In some embodiment, said nucleic acids are DNA, mRNA, tRNA, microRNA, siRNA, or any combination of them.

In some embodiments, said pre-treatment buffer is mixed with said stool sample at a ratio ranging from 1:2 to 4:1 (v/v, buffer to stool). In some embodiments, said stool sample is incubated with said pre-treatment buffer at room temperature. In some embodiments, said stool sample is incubated with said pre-treatment buffer for 10-180 minutes. In some embodiments, the step of centrifugation is performed at 2000-15000 g for 10-120 minutes. In some embodiments, said pre-treatment buffer itself serves as a hybridization buffer for sequence specific capture, eliminating the need for additional solution for hybridization.

Furthermore, herein is provided a kit for removing the interfering substances and inhibitors from a stool sample containing nucleic acids for improving subsequent preparation of nucleic acids from said stool sample, the kit comprising a pre-treatment buffer containing acetated salt(s) and guanidine thiocyanate, centrifuge tubes, and instruction for use. Various types of centrifugations tubes are available for inclusion in said kit, for example those commercially available from a number of suppliers. In some embodiments, said acetate salt(s) is, one of the following or in combination, but not limited to, sodium acetate, potassium acetate, ammonium acetate, and lithium acetate, wherein the preferred final concentration of said acetate salt(s) is 50 mM or more after mixing said pre-treatment buffer with said stool sample. In some embodiments, the preferred final concentration of said guanidine thiocyanate is 2.0M or more after mixing said pre-treatment buffer with said stool sample.

Additional embodiments will be apparent to persons skilled in the relevant art based on the teachings contained herein.

BRIEF DESCRIPTION OF FIGURES

FIG. 1. Real-time PCR amplification curves for quantification of DNA extracted from stool samples that were pre-treated with two different pre-treatment buffers, respectively. (A) the stool sample was pre-treated by Buffer A that contained acetate salts; and (B) the stool was pre-treated with Buffer B that contained no acetate salts.

DETAILED DESCRIPTION

Definitions

To facilitate an understanding of the present invention, a number of terms and phrases are defined below. Additional definitions are set forth throughout the detailed description.

As used herein, "a" or "an" or "the" can mean one or more than one. For example, "a" pen can mean one pen or a plurality of pens.

As used herein, an "interfering substance" means any atom, ion, molecule, compound, substance, or composition, or combination thereof, that acts to decrease the quantity and/or purity of nucleic acids extracted from a sample by a nucleic acid extraction and purification method, either directly or indirectly, with respect to the quantity and quality when the interfering substance is absent.

As used herein, an "inhibitor" means any atom, ion, molecule, compound, substance, or composition, or combination thereof, that acts to decrease the activity, precision, or accuracy of an assay, either directly or indirectly, with respect to the activity, precision, or accuracy of the assay when the inhibitor is absent.

As used herein, the term "impurity" means both interfering substance and inhibitor.

As used herein, the term "pre-treatment" means that before extraction of nucleic acids from a sample containing nucleic acids, said sample is mixed and incubated with a buffer, leading to precipitation of certain substances in said sample, followed by pelleting any precipitates and solid matter by centrifugation; thereafter the supernatant containing nucleic acids is transferred to another container to separate said supernatant from said pellet.

As used herein, the term "sample" is used in its broadest sense. In one sense, it is meant to include a specimen or culture obtained from any source, as well as biological and clinical samples. Biological samples may be obtained from animals and encompass fluids, solids, tissues, and gases. Clinical samples may be obtained from human and include tissues, blood products such as plasma, serum, urine, semen, cerebrospinal fluid, sputum, smears and the like. Clinical samples also include fecal materials. Such examples are not however to be construed as limiting the sample types applicable to the present invention.

As used herein, the term "polymerase chain reaction" ("PCR") refers to the method of K. B. Mullis U.S. Pat. Nos. 4,683,195, 4,683,202, and 4,965,188, that describe a method for increasing the concentration of a segment of a target sequence in a mixture of genomic or other DNA or RNA, without cloning or purification. "PCR" generally involves the use of a nucleic acid sequence as a template for producing a large number of complements to that sequence. The template may be hybridized to a primer having a sequence complementary to a portion of the template sequence and contacted with a suitable reaction mixture including dNTPs and a polymerase enzyme. The primer is elongated by the polymerase enzyme, producing a nucleic acid complementary to the original template. For the amplification of both strands of a double stranded nucleic acid molecule, two primers may be used, each of which may have a sequence that is complementary to a portion of one of the nucleic acid strands. The strands of the nucleic acid molecules are denatured, for example, by heating, and the process is repeated, this time with the newly synthesized strands of the preceding step serving as templates in the subsequent steps. A polymerase chain reaction (PCR) amplification protocol may involve a few to many cycles of denaturation, hybridization and elongation reactions to produce sufficient amounts of the desired nucleic acid. Those of skill in the art will understand the term "PCR" encompasses many variants of the originally described method using, e.g., real time PCR, nested PCR, reverse transcription PCR (RT-PCR), single primer and arbitrarily primed PCR, etc.

As used herein, the term "enzymatic-based assay or analysis" refers to any method of determining the quantity and nucleotide composition of nucleic acids of interest by using enzyme(s). For example, enzymatic-based assays include, but are not limited to, DNA sequencing methods, probe hybridization methods, polymerase chain reaction (PCR), described above; branched hybridization methods (e.g., Chiron, U.S. Pat. Nos. 5,849,481, 5,710,264, 5,124, 246, and 5,624,802, herein incorporated by reference in their entireties); rolling circle replication (e.g., U.S. Pat. Nos. 6,210,884, 6,183,960 and 6,235,502, herein incorporated by reference in their entireties); molecular beacon technology (e.g., U.S. Pat. No. 6,150,097, herein incorporated by reference in its entirety); ligase chain reaction (e.g., Baranay Proc. Natl. Acad. Sci USA 88, 189-93 (1991), herein incorporated by reference in their entireties).

EMBODIMENT OF THE TECHNOLOGIES

The sample containing nucleic acids can contain the impurities that interfere with nucleic acid extraction and inhibit enzymatic reactions. In particular, impurities of this kind inhibit the enzymatic activity of enzymes, e.g., those that are used for polymerase chain reaction (PCR) and various enzymatic-based nucleic acid analysis assays. The sample is obtained from one of the following sources or in combination, but not limited to, human or animal tissues; cell cultures; bone marrow; human or animal body fluids such as blood, serum, plasma, urine, semen, cerebrospinal fluid, sputum, and smears; parts of plants, and plant extracts.

The sample can also be fecal material. Stool samples are the most complicated biological samples. Food debris, digestive metabolites, and many other substances in stool can be the impurities that affect nucleic acid extraction and inhibit enzymatic-based nucleic acid analysis assays such as PCR.

For example, polysaccharides are impurities that can adversely affect nucleic acid extraction and inhibit enzymatic-based nucleic acid analysis. Stool contains a huge amount of polysaccharides resulted from foods. The presence of a large amount of polysaccharides makes stool sample highly viscous. The high viscosity of a stool sample is an obstacle to stool nucleic acid preparation, especially when a magnetic-bead-based method is used in nucleic acid extraction because it is difficult to recover the beads and to effectively remove impurities such as fat, lipids, and proteins when the sample viscosity is high. The impurities, in turn, can cause beads aggregation, making the beads un-recoverable and un-useful.

CTAB precipitation and phenol/chloroform extraction have been used to remove the impurities from a sample containing nucleic acids, but they are generally less effective in removing impurities from a highly complex sample such as stool, especially when the sample is large. Other reagents are also used to precipitate polysaccharides and known precipitating agents include quaternary amine salts (U.S. Pat. No. 3,119,812); aluminum salts (U.S. Pat. No. 4,051, 317); amine salts (U.S. Pat. No. 4,254,257); alkaline in the presence of divalent cations (U.S. Pat. No. 3,382,229), and isopropanol and quaternary compound (U.S. Pat. No. 4,053, 699). All of above reagents require relatively high concentration of toxic salts or the use of organic solvents that are not compatible with following nucleic acid extraction and analysis.

In one preferred embodiment, the present invention provided a pre-treatment buffer containing acetate salt(s) to remove impurities including polysaccharides from a sample containing nucleic acids, while retaining nucleic acids in solution. Specifically, the sample is first mixed and incubated with the buffer, leading to precipitation of the impurities. Then the precipitates are pelleted together with all other solid particles (if present) by a single centrifugation operation, yielding more clarified supernatant containing nucleic acids. Thereafter, the supernatant is separated from the pellet by transferring the supernatant to another tube (liquid container). Nucleic acids are extracted from the supernatant that has been separated from the pellet by a nucleic acid extraction and purification method. It is noted that the choice of salts is, but not limited to, sodium acetate, potassium acetate, ammonium acetate, lithium acetate, and other soluble acetate salts.

In some preferred embodiments, the pre-treatment buffer also contains reagent(s) to facilitate the extraction of nucleic acids, which is, but not limited to, guanidine chloride, urea, sodium chloride, potassium chloride, and soluble phosphate salts; And the final concentration of some reagent(s) is at least 1.0M, wherein for other reagent(s), the preferred concentration is from about 2.0M to 3.0M after mixing with said sample. In another preferred embodiment, said reagent(s) is guanidine thiocyanate and the final concentration of guanidine thiocyanate is from about 2.0M to 3.0M after mixing with said sample. In another preferred embodiments, the pre-treatment buffer that contains guanidine thiocyanate acts as the hybridization buffer when sequence specific capture was used for extraction and purification of nucleic acids. As a result, there is no need for additional solution for hybridization. In some preferred embodiments, guanidine thiocyanate improves lysis of said sample and protects nucleic acids from degradation. The current invention is especially useful when nucleic acids are extracted from a large amount (volume) of stool sample because it resulted in a highly concentrated and purified nucleic acid preparation with a small final elution volume. In some preferred embodiments, the use of the invented pre-treatment buffer simplified the stool sample preparation process before nucleic acid extraction since only one centrifugation step is involved. For example, when treating stool samples with the invented pre-treatment buffer, only one centrifugation step is required to pellet both food debris and precipitates.

The current invention also embodied a system that contains minimized steps for nucleic acid extraction and purification from crude biological samples like stool. The system includes only one centrifuge step to remove solid matter (if present) from sample along with precipitated impurities. In some embodiments, the system also provides automated nucleic acids preparation using sequence specific capture with the oligonucleotide probe conjugated magnetic beads. In some preferred embodiments, nucleic acids from 0.5 gram or more of stool is extracted, purified, and eluted into as little as, for example, 40 μL elution buffer, wherein the eluted nucleic acids preparation is ready for enzymatic-based analysis without detectable inhibitory effects. In some embodiments, the nucleic acids targets captured by oligonucleotide probe conjugated magnetic beads, are used directly in enzymatic-based analysis assays without eluting them off the beads.

The current invention also embodied a kit for recovering nucleic acids from crude samples like stool with a minimized amount of impurities. The kit contains a pre-treatment buffer, tubes and instruction of use. The kit is most useful for recovering cancer or disease related nucleic acid sequences from a large volume of crude sample, wherein the resulting nucleic acids preparation is in a small volume and contains a minimized amount of inhibitors so that enough nucleic acids could be loaded into enzymatic-based nucleic acid analysis assays like PCR without detectable inhibitory effects. Any suitable tubes from commonly available suppliers can be included in the kit. Any commercially available magnetic bead handling system and consumables like plates and reservoirs can be used together with the kit.

EXPERIMENTS

Example 1

Stool sample is collected from a male adult volunteer. About 15 grams of stool sample was placed in a tube containing 30 mL of preservation buffer developed by GLC Biotechnology, Inc. After homogenization, homogenized stool is aliquoted into two 20 mL portions. One portion of homogenized stool is mixed 1:1 with Buffer A, which contains 5M guanidine thiocyanate, 100 mM sodium acetate, 200 mM potassium acetate, and 100 mM Tris. pH was adjusted to about 8.5. The other portion of homogenized stool was mixed 1:1 with Buffer B, which contained 5M guanidine thiocyanate, and 100 mM Tris. pH was adjusted to about 8.5. After thorough mixing, the mixtures were incubated at room temperature for 2 hours before centrifugation at 10800 g for 20 minutes. After centrifugation, supernatants are aliquoted into 4 mL portions (equivalent to 1 gram of stool each) for DNA extraction.

After denaturation, the denatured stool samples were then loaded into a deep-well plate wherein each well contained 20 μL DNA probe conjugated magnetic beads. Because both Buffers A and B contained 5M guanidine thiocyanate, both of them could sever as the hybridization buffer for sequence specific capture without a need for additional buffers for hybridization. Sequence specific capture was then performed. In general, sequence specific capture with oligonucleotide conjugated magnetic beads (hybridization), beads collection and transfer, beads washing, and DNA elution were all performed automatically on the automated platform without further human intervention. Captured stool DNA was eluted in tris buffer with a concentration of 5 mg stool equivalent per microliter (5 mg/μL), which was ready to use for analysis by enzymatic-based methods such as polymerase chain reaction (PCR).

FIG. 1 displayed the result of PCR amplification of captured DNA from the stool samples treated by either Buffer A or Buffer B, wherein a sequence of human beta-actin gene (ACTB) was extracted and amplified. The PCR condition is described as below: precision-melt HRM Master Mix (final concentration 1×, Bio-rad), primers (final concentration 0.5 μM), and stool DNA (equivalent to 20 mg stool) were mixed and the total PCR volume was adjusted to 20 μL with nuclease free water. The sequences of the forward and reverse primers were: 5'-TTGCTTTTTCCCA-GATGAGC-3' (SEQ ID NO 1) and 5'-ACACTCCAAGGC-CGCTTTAC-3' (SEQ ID NO 2), respectively. Real-time qPCR was performed on Light-cycler 480 II real-time cycler (Roche). The qPCR protocol is described as below: 95° C. for 10 min, followed by 50 cycles of 95° C. for 20 seconds, 60° C. for 30 seconds, and 72° C. for 45 seconds, followed by a 72° C. extension for 3 minutes. Then, a high-resolution-melting (HRM) melting curve was generated for quality control with the following settings: 95° C. for 1 minute, 60° C. for 1 minute, then a melting curve was obtained from 60° C. to 95° C. with an increment of 0.02° C./second and 25 acquisitions/° C. The final result was analyzed with Light-cycler 480 software from Roche.

As shown in FIG. 1, no observable amplification was seen when Buffer B (without acetate salts) was used to pre-treat stool, but strong PCR amplification was observed when Buffer A (with acetate salts) was used to pre-treat stool, demonstrating the effectiveness of using invented buffer in extracting highly purified DNA from stool.

CITATION LIST

Patent Literature

Kary B. Mullis et al., U.S. Pat. No. 4,683,195 A 1986
Kary B. Mullis., U.S. Pat. No. 4,683,202 B1 1985
Kary B. Mullis et al., U.S. Pat. No. 4,965,188 A 1987
Michael S. Urdea et al., U.S. Pat. No. 5,849,481 A 1995
Michael S. Urdea et al., U.S. Pat. No. 5,710,264 A 1995
Michael S. Urdea et al., U.S. Pat. No. 5,124,246 A 1989
Michael S. Urdea et al., U.S. Pat. No. 5,624,802 A 1995
Paul M. Lizardi, U.S. Pat. No. 6,210,884 B1 1998
Paul M. Lizardi, U.S. Pat. No. 6,183,960 B1 1998
Sherman Weissman et al., U.S. Pat. No. 6,235,502 B1 1999
Sanjay Tyagi et al., U.S. Pat. No. 6,150,097 A 1997
Rogovin S. Peter et al., U.S. Pat. No. 3,119,812 A 1962
Gordon A. Towle, U.S. Pat. No. 4,051,317 A 1976
Calvin W. Schroeck, U.S. Pat. No. 4,254,257 A 1979
John T. Patton et al., U.S. Pat. No. 3,382,229 A 1963
Patrick T. Cahalan et al., U.S. Pat. No. 4,053,699 A 1976

Non-patent Literature

Barany F., "Genetic disease detection and DNA amplification using cloned thermostable ligase", Proc Natl Acad Sci USA. 1991 Jan. 1; 88(1):189-93.

What is claimed is:

1. A method for isolation and purification of nucleic acids from a stool sample containing said nucleic acids comprises the steps of:
   (a) mixing and incubating said stool sample with a pre-treatment buffer that contains acetate salt(s) and guanidine thiocyanate; and
   (b) centrifuging said stool sample to pellet solid matter and precipitates in said stool sample after said step of (a); and
   (c) transferring the supernatant created from said step of (b) to another liquid container; and
   (d) performing nucleic acids extraction and purification from said transferred supernatant after said step of (c).

2. The method of claim 1, wherein said acetate salt(s) in said pre-treatment buffer is one of the following or in combination, but not limited to, sodium acetate, potassium acetate, ammonium acetate, and lithium acetate, and the concentration of said acetate salt(s) in said stool sample is 50 mM or more after mixing said pre-treatment buffer with said stool sample.

3. The method of claim 1, wherein the concentration of said guanidine thiocyanate in said stool sample is 1.0M or more after mixing said pre-treatment buffer with said stool sample.

4. The method of claim 1, wherein said step of nucleic acids extraction and purifications is sequence specific capture with magnetic beads.

5. The method of claim 1, wherein said nucleic acids are, but not limited to, DNA, mRNA, tRNA, microRNA, siRNA, or any combination of them.

* * * * *

SEQUENCE LISTING

<160> NUMBER OF SEQ ID NOS: 2

<210> SEQ ID NO 1
<211> LENGTH: 20
<212> TYPE: DNA
<213> ORGANISM: Homo sapiens

<400> SEQUENCE: 1 ttgcttttc ccagatgagc                20

<210> SEQ ID NO 2
<211> LENGTH: 20
<212> TYPE: DNA
<213> ORGANISM: Homo sapiens

<400> SEQUENCE: 2
acactccaag gccgctttac               20